United States Patent [19]

Pioger et al.

[11] Patent Number: 5,725,566
[45] Date of Patent: Mar. 10, 1998

[54] METHOD AND KIT FOR PASSIVATING PROBES FOR ACTIVE IMPLANTABLE MEDICAL DEVICES

[75] Inventors: Guy Pioger, Paris; Jean-Francois Ollivier, Guyancourt; Alain Ripart, Gif Sur Yvette, all of France

[73] Assignee: ELA Medical S.A., Montrouge, France

[21] Appl. No.: 760,442

[22] Filed: Dec. 6, 1996

[30] Foreign Application Priority Data

Dec. 8, 1995 [FR] France ................... 95 14580

[51] Int. Cl.$^6$ ............................................. A61N 1/05
[52] U.S. Cl. ................................. 607/125; 128/897
[58] Field of Search ............................... 128/897, 898; 607/115, 116, 122, 125, 126

[56] References Cited

U.S. PATENT DOCUMENTS

| | | | |
|---|---|---|---|
| 4,917,104 | 4/1990 | Rebell | 128/722 |
| 5,135,490 | 8/1992 | Strickland | 128/898 |
| 5,213,115 | 5/1993 | Zytkovicz et al. | 128/898 |
| 5,255,678 | 10/1993 | Deslaurigrs et al. | 607/122 |
| 5,423,880 | 6/1995 | Nyman et al. | 607/122 |
| 5,476,005 | 12/1995 | Lindegren et al. | 73/40 |

FOREIGN PATENT DOCUMENTS

| | | | |
|---|---|---|---|
| 0589182 A1 | 3/1994 | European Pat. Off. | A61N 1/05 |
| 0622089 A2 | 11/1994 | European Pat. Off. | A61N 1/05 |
| 0635281 A1 | 1/1995 | European Pat. Off. | A61N 1/08 |
| WO94/22525 | 10/1994 | WIPO | A61N 1/05 |
| WO95/11056 | 4/1995 | WIPO | A61N 1/05 |

OTHER PUBLICATIONS

Daubert, et al, "Que Faire Face aux defaillances des sondes Telectronics Accufix?" *Stimucoeur*, vol. 23, No. 1, pp. 27–28 (1995).

Dodinot, "Ouvrons l'oeil", *Stimucoeur*, vol. 23, No. 1, pp. 39–44 (1995).

Parsonnet "The Retention wire fix" *Pace*, vol. 18, May 1995, Part 1, pp. 955–957.

Lloyd et al. "Atrial 'J' Pacing Lead Retention Wire Fracture Radiographic Assessment, Incidence of Fracture, and Clinical Management" *Pace*, vol. 18, May 1995, Part I pp. 958–964.

*Primary Examiner*—William E. Kamm
*Attorney, Agent, or Firm*—Orrick Herrington & Sutcliffe, LLP

[57] ABSTRACT

Process and kit for passivating in situ a tip of a probe for an active implantable medical device, particularly for a cardiac pacemaker probe. The probe (10) is of the type comprising a hollow insulating sheath (12) made of a supple material having an internal conductor (14) terminated at its distal extremity by an electrode (16), an axial canal (18) along its length, and a support element (22) at its distal extremity in the neighborhood of the electrode, particularly a metallic filament or blade for shaping or reinforcing the distal extremity (20) of the probe. The support element is of a rigidity that is greater than the combination of the sheath and the internal conductor. The process of the invention is characterized by injection of a solidifiable material (48) in a fluid state in the internal volume of the sheath to fill the region of the distal extremity in a manner so as to coat at least a part of the support element and then to change the state of the solidifiable material to a solid, so as to immobilize the coated support element in the sheath. Advantageously, the injection is driven inside an injection tube (26) which is introduced inside the sheath and sealed in an hermetic manner to the sheath. The kit includes the equipment necessary to inject the solidifiable material into the probe in a passivation procedure.

20 Claims, 1 Drawing Sheet

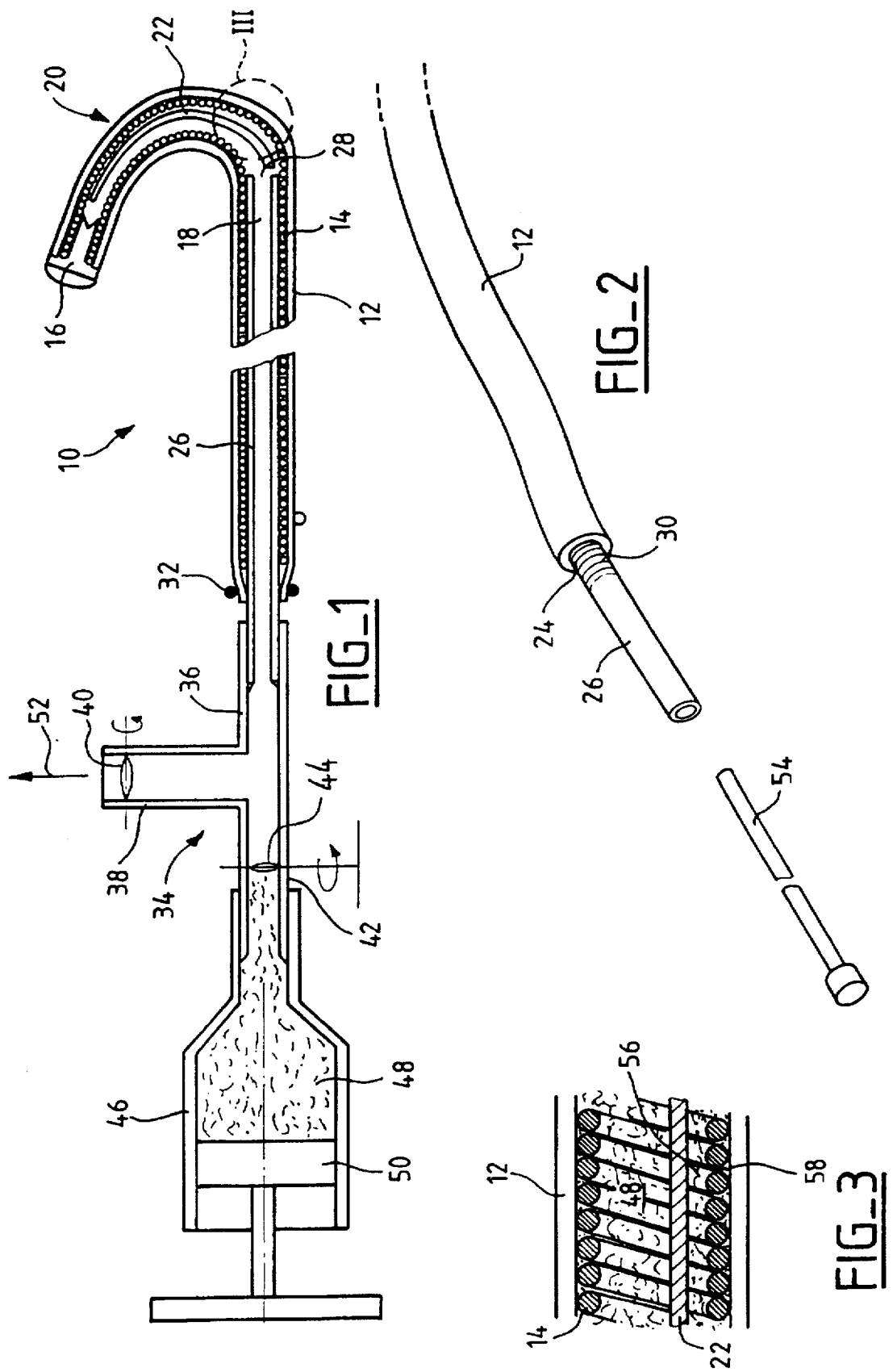

METHOD AND KIT FOR PASSIVATING PROBES FOR ACTIVE IMPLANTABLE MEDICAL DEVICES

FIELD OF THE INVENTION

The present invention concerns passivating in situ a tip of a probe of an active implantable medical device, more particularly, a cardiac pacemaker probe having a preformed shape.

BACKGROUND OF THE INVENTION

There is a known type of probe for use with cardiac pacemakers comprising a insulating sheath made of a supple material and having an internal volume and an internal conductor terminated at its distal extremity by an electrode. The probe has along its length an axial canal containing, at its distal extremity, in the neighborhood of the electrode, a support element. The support element may be a metallic wire or blade that functions to give a particular shape and/or to reinforce structurally the extremity of probe. The support element is provided with a greater rigidity than the combination of the sheath and the conductor. Other probe configurations are known where the support element is situated in the sheath, but exterior to the axial canal. Probes are also sometimes referred to as leads or catheters, particularly endocardial leads that couple a pacemaker to cardiac tissue for sensing and pacing cardiac activity.

For convenience, the terms "blade" and "metallic blade" used herein shall refer to the relatively rigid support element or structure that is used to reinforce and/or maintain a desired shape of the probe distal extremity, although this term is not restrictive, in that the support element is able to have, for example, a filament form or be constructed of a material other that metal.

It has recently observed that some probes of this type have presented, over the long term, a risk of fracture of the blade. The fracture of the blade, considering its relative stiffness and the fragility of the material of the sheath (which is generally a polyurethane material), can result in the blade or some part of it piercing the sheath, and even protruding from the sheath, with a consequent risk of perforating the heart.

In addition, even if the blade remains intact, due to the fact of its curved or winding shape and rigidity, an attempt to remove or extract the probe by traction presents a risk of tearing an arterial or cardiac wall.

These risks have been described and studied in various publications, particularly those by J. C. Daubert et al. "Que faire face aux défaillances des sondes Telectronics Accufix?", Stimucœur 1995, volume 23, n° 1 pp. 27–28; B. Dodinot, "Ouvrons l'œil". Stimucœur 1995 volume 23, n° 1 pp. 39–44; Mr. A. Lloyd et al. "Atrial "J" Pacing Lead Retention Wire Fractures: Radiographic Assessment, Incidence of Fracture, and Clinical Management", PACE, Vol. 18, May 1995, pp. 958–964; and V. Parsonnet, "The Retention Wire Fix", PACE, Vol. 18, May 1995, pp. 955–997.

OBJECTS AND SUMMARY OF THE INVENTION

It is, therefore, an object of the present invention to propose an intervention to render passive the probe, that is to immobilize the potentially harmful support element by coating it in a manner to protect the sheath of the probe in case of a fracture of the blade, thereby minimizing the likelihood that the blade will pierce and protrude from the sheath. The probe is thus rendered relatively harmless and can be left in place (still used or not used), or extracted without a significant consequential risk of damage if the metallic blade should break during the intervention.

To this end, the present invention broadly concerns the injection into the internal volume of the sheath of probes of the aforementioned type, to deliver to at least the region of the distal extremity of the internal volume, a solidifiable material susceptible of changing from a liquid state to a solid state. This solidifiable material is injected in a manner that it will coat, and when solidified, immobilize, at least a part of the support element.

According to one preferred embodiment, before the injection, the pressure inside the sheath is reduced to create a partial vacuum in the internal volume of the sheath. This is done to facilitate the injection by fixing the vacuum and opening the vacuum to the supply of solidifiable material so that the material is aspirated into the sheath by a pressure gradient.

In another embodiment, after the injection, there is a step of compacting the injected solidifiable material to assist in forcing the solidifiable material to coat the support element. This is preferably performed by introducing a styler into the internal volume of the tube to push mechanically the solidifiable material into the distal portion of the probe and around the support element. Once compacted, the solidifiable material is then changed to its solid state.

In yet another embodiment, prior to the injection of the solidifiable material, an injection tube is introduced inside the sheath and hermetically connected to the sheath, such that the injection of the solidifiable material is driven through the injection tube. In this embodiment, before its introduction into the sheath, the injection tube is preferably cooled to a temperature below room temperature, in a manner to render more liquid the solidifiable material during the injection. It also is envisioned that, after the injection, the injection tube will be disconnected and extracted from the sheath before the injected solidifiable material is changed to a solid state.

In yet another embodiment, the hermetic quality of the sheath, that is whether or not the sheath is intact and impervious to body fluids such as blood, is tested prior to proceeding with the passivation intervention. This may be achieved by attempting to establish a partial vacuum in the internal volume of the sheath. If blood or body fluids are aspirated during this test, then the hermetic quality is not good. The quality can then be relatively assessed for determining whether or not to proceed with the intervention. If the quality is good, then the intervention can proceed.

In yet another embodiment, there also is an installation of an obturator (or plug) in the sheath and ligating the sheath filled with the solidifiable material to the obturator. It should be understood that the obturator could be the proximal portion of the injected solidifiable material which is injected in a sufficient quantity to fill the sheath and solidified.

Preferably the solidifiable material is a radio opaque silicone resin that is injected in a fluid state and can be changed to a solid state in the sheath. The change of state of the solidifiable material is also referred to as curing or vulcanization or hardening as these terms are generally known to a person of ordinary skill in the art for the particular material used.

One aspect of the invention is thus directed to a process for passivating in situ a probe. Another aspect of the invention is directed to a passivated probe. Yet another aspect of the invention is directed to a kit containing the equipment needed to perform the passivating process in situ.

BRIEF DESCRIPTION OF THE DRAWINGS

Others characteristics and advantages of the invention will appear in the discussion of a preferred embodiment of the invention, made with reference to the detailed description and the drawings annexed, in which like reference numerals refer to like elements and in which:

FIG. 1 is a schematic cross sectional view of a probe and the equipment used to perform its passivation in accordance with a preferred embodiment of the present invention;

FIG. 2 is a perspective cut-away view illustrating some of the equipment and process of the present invention; and FIG. 3 is an enlarged cross sectional view of detail area III of FIG. 1, after the solidifiable material has been injected and solidified.

DETAILED DESCRIPTION OF THE DRAWINGS

Referring to FIG. 1, the reference 10 designates a probe of the type whose disadvantages have been described in the various aforementioned articles, particularly an atrial probe in shape of J, also referred to as an atrial J probe. The J shape is provided to facilitate the placement of the electrode 16 in the right atrium, and it is typically obtained by a rigid support element or blade 22 inserted inside the insulating sheath 12. (It is noted that there also exists a technique of pre-forming the insulating sheath and/or the internal conductor to have the J shape, but these constructions do not have the additional rigid support element and therefore do not present the risk of injury that the present invention is directed to overcome).

The reference 12 thus designates the external sheath, which is generally made of a soft, flexible (supple) material, such as 25 a polyurethane. Sheath 12 encloses an internal conductor 14, which is spiral wound inside the sheath 12 and terminates at a distal extremity in an electrode 16. In the case of a bipolar probe (not shown), there are two spiral conductors, with the rest of the construction being essentially the same. The probe 10 typically has lodged in its internal volume 18, in the distal curvature part designated by reference 20, a metallic blade 22 for reinforcing the probe distal part 20, and/or for maintaining the desired shape, e.g., of a J.

There exists another type of probe which contains the same type of blade (not shown), but which blade is situated at the exterior of the axial canal.

The rupture or fracture of blade 22 can have very serious consequences if it crosses the spiral conductor 14 and pierces the insulating sheath 12. This is because sheath 12 is made of a material, a polyurethane, which is relatively sensitive to risks of tearing by such a hard metallic object. In some configurations, the blade 22 can contact the wall of the atrium and possibly perforate the cardiac wall or the aorta, with a risk of fatality in case of a hemorrhage. The broken fragment that has caused the protrusion can even detach from the probe and become entrained in the pulmonary artery.

The extraction of a such probe by traction presents an additional risk of tearing the atrial wall due to the rigidity of the blade 22. This is so whether or not the blade is intact during the extraction.

Furthermore, removal of the probe by open heart surgery contains a different set of risks.

Thus, it can be as harmful, if not more harmful, to attempt to extract the probe as it is to leave it in place.

The invention proposes to overcome these problems and, essentially, to immobilize the metallic blade 22 by injection of a solidifiable material, typically a silicone, inside the probe to coat the blade. This renders the probe harmless and allows the probe to remain in place or, if one wishes, to attempt an extraction with a significantly lesser degree of risk, as well as to permit continued use of the probe.

In accordance with one embodiment of a passivating process of the invention, the first stage is to test the hermetic quality of the probe. To this end, after disconnecting the pacemaker from the proximal part of the probe (that is to say decoupling the pacemaker from the proximal electrical connector), one connects the proximal extremity to a transparent lumen (such s a polyurethane tubing, not shown) which is in turn connected to an aspirating pump or valved vacuum supply (represented in FIG. 1 by arrow 52). After some time of an applied vacuum, if blood is not aspirated into the lumen, the probe is considered to have a good hermetic quality and one can continue the passivation. In the opposite case, if blood is aspirated into the lumen, one can consider to perform a classic extraction procedure, or to continue nevertheless the intervention despite the imperfect hermetic seal. In this latter case, one can, if one decides to proceed with the injection of the silicone, to follow its progression inside the probe by having taken care to precede this injection with a small quantity of a radio opaque liquid. This will allow one to observe the progress and determine whether or not it is successful in injecting the solidifiable material in the desired locations(s).

The next stage occurs after having taken away the aspiration system, and is to section probe 10 at area 24, to remove the electrical connector near the proximal part of the probe. The section at area 24 is made at a known distance from the connector, in a manner to be able to determine with precision the exact remaining length of the probe. At the opening 24 thus created, one introduces in the internal canal of probe 10 an injection tube 26, such as a flexible metallic tube. One such tube, for example, is a tube having dimensions of 0.5 mm×0.4 mm×500 mm which is made of 304 stainless steel which has been stretched hard with a cleaned tip, which tubing is available from Microfil ITS.

A variant of the aforementioned embodiment, which does not involve sectioning the connector, is to splice into the sheath near the connector, then to connect the splice to the aforementioned aspiration equipment and then to the injection equipment which is described below.

For the introduction of tube 26, the physician can help guide the tube 26 in by using a styler 54 (FIG. 2) introduced in the sheath 12. Such a styler 54 should have a round distal extremity and slightly protrude about the distal extremity 28 of the tube 26. This provides a better introduction of tube 26 in the sheath cavity 18. The tube 26 is preferably introduced inside such that its distal extremity 28 is placed approximately at the vicinity of the metallic blade 22. The adjustment of the length of tube 26 can be advantageously obtained by use of a colored mark 30 (FIG. 2), such that tube 26 is advanced to the place of the opening 24, until mark 30 is partially hidden by the sheath 12, thereby indicating that the distal extremity 28 of the tube 26 is near the blade 22. This can be done by placing the mark 30 an appropriate distance from the distal end of tube 26 with knowledge of the length of probe 10 remaining. At this stage, the physician seals hermetically the proximal extremity 24 of the probe 10 sheath 12 to tube 26 by a ligature 32. The ligature can be performed by tying a suture or a clip or staple or other device sufficient to obtain an effective seal. This ligation also insures blocking the translation of tube 26 relative to the probe 10 during the intervention.

Next, a T connector 34 is secured to the proximal extremity of the tube 26 extending out of sheath 18. T connector 34 may be, for example, a three way connector made of a polycarbonate and having male Luer tip, which is available from Bioblock, product ref. A13600. Such a T connector has a first branch 36 frictionally connected in a tight manner to the tube 26, a second branch 38 which can be selectively opened and closed by a maneuverable valve connector 40, and a third branch 42 which can be selectively opened and closed by a maneuverable valve connector 44. Initially, valve connectors 40 and 44 are maintained in a closed position.

The branch 42 is then connected to a syringe 46 (for example, frictionally fitted to a syringe having a volume of 3 cc, manufactured by EFD, product ref. 5109AUV-B.) The syringe is loaded with a volume of solidifiable material 48, such as a silicone resin 48. Syringe 46 has a piston 50 that may be actuated to inject the material 48. This silicone resin is, for example, a medical grade silicone paste known as Raumedic SI 1511, available from Rehau, which is mixed with a toluene or an equivalent additive, which functions to increase the fluidity of the paste, and loaded with radio opaque particles. The radio opaque particles allow one to follow the injection process under an imaging device [amplifier of brilliance—TRANSLATION?] and to control finely the complete coating of the metallic blade by confirming the hermetic quality of the sheath as the silicone is injected. The vulcanization of the silicone paste makes it change from a liquid-viscous state to a solid-supple state, the latter state corresponding to a Shore hardness of approximately 30 to 80.

The injection stage can be realized either by a pistol type grip operated by the operator (for example, an injection pistol known as the DispensGun, having a 3 cc volume, available from EFD, product ref. DG3), or by an automatic system controlled by pressure. The automatic pressure system presents the advantage of the possibility to control, according to the time of flow, the progression of the injection in the tube (for example, a dose applicator timed at 0.07 to 7 bars, which device is available from EFD, product ref. 1500 XL, with an adapter for a 3 cc syringe, product ref. 1000Y5152-6).

In operation, the branch 38 is connected to a vacuum source (schematically represented on FIG. 1 by the arrow 52) and the connector 40 is opened. This has for an effect to create a partial vacuum inside the probe 10, the hermetic quality of which has already been determined beforehand. This vacuum will facilitate the flow of the solidifiable material into the sheath and will minimize the formation of air bubbles resulting from the injection.

Next, the valve connector 40 is closed and the valve connector 44 is opened to the vacuum. This has for its consequence, by effect of the vacuum, to aspirate the solidifiable material 48 through the tube 26 then through to the distal part, thus coating the metallic blade 22 along its length.

If need be, one can assist or perfect the filling process by acting on the piston 50. Optionally, one also can facilitate the filling process by compressing slightly the injected material, for example, by pushing a stylet 54 in the tube 26, after having removed the piston 50. It should be understood that the valve connector 44 should be closed first, so that, for example, the stylet or other object can be inserted through valve connector 44, or the T connector 34 can be removed before passing a compacting styler 54 into the sheath.

Advantageously, before its introduction, the injection tube 26 can be maintained at a low temperature (that is to say to an appreciably lower temperature than room temperature or the body temperature, for example, on the order from +2 to +5° C., to maximize the fluidity of the silicone paste to be injected.

In an alternate embodiment, and for safety reasons, it is possible to cover the probe with a second sheath (not shown), in a manner to insure a supplemental protection over the exterior of probe 10.

The intervention is terminated by waiting for the reticulation (that is, the vulcanization, solidifying or setting) of the silicone. To accelerate the reticulation, one can possibly preliminary inject water at the extremity of the tube and/or insert after the injection a pre-heated shaft or heated stylet 54 having dimensions corresponding to the exterior of the tube 26, so that the heat is transferred to the resin by the metallic spiral of the conductor 14. For example, the heat could be transferred to the proximal portion of conductor 14, and thermally conducted along conductor 14 to its distal portion where the heat is then transferred to the resin to accelerate the reticulation.

As a result of the intervention, the metallic blade 22 is coated and immobilized.

It is noted that there is not only a filling of the space situated between the blade 22 and the spiral windings of the conductor 14 (as illustrated at 56 on FIG. 3), but also a filling of the space 58 between the spirals 56 and even between the spirals 56 and the sheath 12. This has for an effect a mechanical encasement of the conductor 14 in addition to the immobilization of the blade 22. One thus minimizes the risk of the blade penetrating through the hardened silicone mass coating the blade, the silicone encased conductor, and the sheath, and perforating the heart.

It suffices then to ligate the injected, hardened silicone plug to the proximal extremity 24 of the probe 10 and to abandon the probe in place, unless one wishes to extract the probe or to reuse the probe by connecting it again to an appropriate adapter (for example a model XT3 adapter available from ELA Medical) which need to replace a sectioned electrical connector.

In all cases, the present invention advantageously benefits from a repaired probe whose distal part has not lost its flexibility; and the silicone fluid used, once solidified, keeps indeed a maximal suppleness such that one does not create new fragile zones while minimizing risk of injury to the patient.

In another aspect of the invention, a kit is provided for use in passivating installed probes. The kit comprises a T connector 34, an injection tube 26, a lumen having a male Luer tip to connect to a vacuum source, as such sources are typically found in conventional operating rooms, a syringe 46, and a volume of solidifiable material 48, which is preferably premixed and preloaded in the syringe 46. Preferably, the kit also includes one or more stylets 54, which can be variously used for inserting tube 26 inside the sheath interior volume 18, for compacting the injected solidifiable material, and optionally for heating the injected solidifiable material to cause it to solidify. Also, the kit may contain a suture 32 which may be prethreaded for ligating the sectioned sheath 24 to the tube 26.

This kit can be prepackaged in conventional sterile packaging, so that it preferably contains all of the equipment needed by the physician to perform the passivation intervention of the present invention. In this regard, the kit also could include a tool for sectioning the probe 10, for example, a wire cutting scissors, and a length of transparent tubing t be connected to a vacuum source for aspirating blood or not, to test the hermetic quality of the sheath 18. Alternately, the tube 26 could be separately packaged so that it can be refrigerated separately from other components of the kit prior to insertion. Similarly, the solidifiable material can be separately stored in a container with its components premixed or separated to be mixed immediately prior to use. In such case, in a preferred embodiment, a silicone paste, toluene additive and radio opaque particles are separately stored, mixed immediately prior to use, and then aspirated into the syringe for injection into tube 26. When appropriate, the mixture to be injected also can be refrigerated or otherwise cooled to maintain or enhance its fluidity prior to injection.

One skilled in the art will appreciate that the present invention can be practiced by other than the described embodiments, which are presented for purposes of illustration and not limitation.

We claim:

1. A process of passivating in situ a probe tip of an active implantable medical device, the probe (10) having an insulating sheath (12) made of a supple material, an internal conductor (14) terminated at its distal extremity by an electrode (16), an axial canal (18) defining an internal volume along its length, and a support element (22) at its distal extremity (20) in the neighborhood of the electrode, the support element having a rigidity greater than the combination of the sheath and the conductor for shaping and/or reinforcing the distal extremity, comprising:
   (a) providing a volume of solidifiable material in a fluid state;
   (b) injecting said solidifiable material into the insulating sheath so that the solidifiable material coats at least a portion of said support element; and
   (c) changing the solidifiable material from a fluid state to a solid state, thereby immobilizing at least a portion of said support element inside said sheath.

2. The process of claim 1, further comprising, prior to step (b), establishing a partial vacuum in the internal volume of the sheath.

3. The process of claim 1, further comprising, after step (b), compacting the solidifiable material injected inside said sheath.

4. The process of claim 3 wherein said compacting step further comprises introducing a styler (54) into the internal volume of the tube.

5. The process of claim 1, further comprising prior to step (b), introducing inside the sheath an injection tube (26), and connecting the sheath to injection tube, wherein step (b) further comprises injecting the solidifiable material through the injection tube into said sheath.

6. The process of claim 5, further comprising, prior to introducing the injection tube into the sheath, providing the injection tube with a temperature below room temperature, thereby to render fluid the solidifiable material during its injection.

7. The process of claim 5, further comprising disconnecting and extracting the injection tube out of the sheath prior to step (c).

8. The process of claim 1, further comprising determining whether or not there is a good hermetic quality of the sheath prior to step (b).

9. The process of claim 8, in which determining whether or not there is a good hermetic quality of the sheath further comprises attempting to establish a vacuum in the internal volume of the sheath.

10. The process of claim 9 in which determining whether or not there is a good hermetic quality of the sheath further comprises connecting a transparent lumen to the sheath and examining the lumen for the presence therein of a body fluid in response to an attempted vacuum.

11. The process of claim 1, further comprising, after step (c) installing an obturator and ligating the sheath filled with the solidifiable material.

12. The process of claim 1, in which step (a) further comprises providing a volume of a radio opaque silicone resin.

13. A probe having a blade passivated in accordance with the process of claim 1.

14. A kit for passivation of a cardiac probe installed in a patient, said probe having a proximal end and a distal end, an interior conductor, an exterior sheath, an internal volume extending from said proximal end to said distal end, a support element disposed in the distal end, said support element having a rigidity that is greater than the combination of said sheath and conductor, the kit comprising:

a solidifiable material;

a syringe having an injection chamber to receive said solidifiable material and an output port;

an injection tube having a proximal opening and a distal opening, the injection tube being insertable in the interior volume of said probe; and a T connector having a first branch, a second branch and a third branch, the second and third branches each having a valve for opening and closing said branch;

wherein the T connector first branch frictionally connects to the proximal end of the injection tube, the T connector second branch is adapted to be connected to a vacuum source, and the T connector third branch connects to the syringe output port, and wherein the first and second valves are operable to create a vacuum in said probe interior volume and aspirate the solidifiable material into said probe distal end.

15. The kit of claim 14 further comprising a styler having a dimension suitable to pass interior to said sheath interior volume.

16. The kit of claim 14 further comprising a ligature to connect the sheath to the injection tube.

17. The kit of claim 14 wherein the injection tube further comprises a mark corresponding to a distance between said mark and said tube distal end.

18. The kit of claim 14 further comprising a length of tubing to connect the T connector second branch to a vacuum source.

19. The kit of claim 18 wherein the length of tubing is transparent.

20. The kit of claim 14 further comprising a styler having a dimension suitable to pass interior to said injection tube.

* * * * *

UNITED STATES PATENT AND TRADEMARK OFFICE
CERTIFICATE OF CORRECTION

PATENT NO. : 5,725,566
DATED : March 10, 1998
INVENTOR(S) : Pioger et al.

It is certified that error appears in the above-identified patent and that said Letters Patent is hereby corrected as shown below:

column 1, line 35, delete "that" and insert --than--;
column 1, line 36, after "recently" insert --been--;
column 2, line 22, delete "styler" and insert --stylet--;
column 3, line 33, after "as" delete "25";
column 4, line 12 after "such" delete "s"and insert --as--;
column 4, line 46, delete "styler" and insert --stylet--;
column 6, line 65, after "tubing" delete "t" and replace with "to";
column 7, line 43, delete "styler" and insert --stylet--;
column 8, line 45, delete "styler" and insert --stylet--;
column 8, line 57, delete "styler" and insert --stylet--.

Signed and Sealed this

Fifteenth Day of December, 1998

Attest:

BRUCE LEHMAN

*Attesting Officer*     *Commissioner of Patents and Trademarks*